[12] United States Patent  
Turner

(10) Patent No.: US 10,052,223 B2  
(45) Date of Patent: Aug. 21, 2018

(54) BACK SUPPORT DEVICE

(71) Applicant: Stuart Turner, Annapolis, MD (US)

(72) Inventor: Stuart Turner, Annapolis, MD (US)

(73) Assignee: TURNER INNOVATIVE SOLUTIONS, LLC, Annapolis, MD (US)

( * ) Notice: Subject to any disclaimer, the term of this patent is extended or adjusted under 35 U.S.C. 154(b) by 12 days.

(21) Appl. No.: 15/488,042

(22) Filed: Apr. 14, 2017

(65) Prior Publication Data  
US 2017/0340472 A1 Nov. 30, 2017

Related U.S. Application Data

(60) Provisional application No. 62/343,204, filed on May 31, 2016, provisional application No. 62/468,504, filed on Mar. 8, 2017.

(51) Int. Cl.  
A61F 5/02 (2006.01)  
A61F 5/01 (2006.01)  
(Continued)

(52) U.S. Cl.  
CPC .............. *A61F 5/028* (2013.01); *A41B 1/08* (2013.01); *A41B 9/06* (2013.01); *A41D 13/0155* (2013.01);  
(Continued)

(58) Field of Classification Search  
CPC .. A61F 5/012; A61F 5/02; A61F 5/022; A61F 5/024; A61F 5/026; A61F 5/028; A41D 13/0531  
(Continued)

(56) References Cited

U.S. PATENT DOCUMENTS 3,717,143 A 2/1973 Johnson  
4,120,297 A 10/1978 Rabischong et al.  
(Continued)

FOREIGN PATENT DOCUMENTS

CA 2941872 A1 9/2015  
CN 102247021 A 11/2011  
(Continued)

OTHER PUBLICATIONS

International Search Report for PCT/US2017/035081 (ISA=US) dated Aug. 1, 2017.  
(Continued)

*Primary Examiner* — Keri J Nelson

(57) ABSTRACT

A garment worn on the upper body is provided with a back support system that can be selectively actuated as needed, and otherwise remains relatively unobtrusive when not actuated. The back support system includes a selectively inflatable and deflatable air bladder positioned at a desired location on a rear part of the garment opposite a portion of the wearer's back that needs support. Preferably, the air bladder is disposed within a pocket or compartment, preferably defined on an interior side of the garment, thereby leaving the exterior of the garment relatively unaltered in a visual sense. In a particular example, the air bladder of the present invention has a physical configuration designed to support specific portions of the spinal column as well as adjoining musculature.

30 Claims, 13 Drawing Sheets

(51) Int. Cl.
*A41B 1/08* (2006.01)
*A41B 9/06* (2006.01)
*A41D 13/015* (2006.01)
*A41D 13/05* (2006.01)

(52) U.S. Cl.
CPC .............. *A61F 5/012* (2013.01); *A61F 5/024* (2013.01); *A41B 2400/32* (2013.01); *A41D 13/0531* (2013.01); *A61F 5/02* (2013.01)

(58) Field of Classification Search
USPC ............................... 602/13, 19; 2/DIG. 3, 44
See application file for complete search history.

(56) References Cited

U.S. PATENT DOCUMENTS

| | | | |
|---|---|---|---|
| 4,178,922 | A | 12/1979 | Curlee |
| 4,178,923 | A | 12/1979 | Curlee |
| 4,310,927 | A | 1/1982 | Debose |
| 4,682,587 | A | 7/1987 | Curlee |
| 4,682,588 | A | 7/1987 | Curlee |
| 4,702,235 | A | 10/1987 | Hong |
| 4,703,750 | A * | 11/1987 | Sebastian ................ A61F 5/028 128/DIG. 20 |
| 5,007,412 | A | 4/1991 | Dewall |
| 5,062,414 | A | 11/1991 | Grim |
| 5,072,727 | A | 12/1991 | Aronne |
| 5,205,814 | A | 4/1993 | Lundrigan et al. |
| 5,303,425 | A | 4/1994 | Mele |
| 5,450,627 | A | 9/1995 | Grilliot et al. |
| 5,450,858 | A | 9/1995 | Zablotsky et al. |
| 5,628,721 | A | 5/1997 | Arnold et al. |
| 5,704,904 | A | 1/1998 | Dunfee |
| 6,045,519 | A | 4/2000 | Smith |
| 6,321,388 | B1 | 11/2001 | Hildebrandt |
| 6,564,387 | B1 | 5/2003 | Willoughby |
| 6,629,942 | B1 | 10/2003 | Tubbs |
| 7,001,350 | B2 | 2/2006 | Grosso |
| 7,392,549 | B1 | 7/2008 | Barber |
| 7,591,797 | B2 | 9/2009 | Hakonson et al. |
| 7,871,388 | B2 | 1/2011 | Brown |
| 8,361,003 | B2 | 1/2013 | Reiley |
| 8,663,141 | B2 | 3/2014 | Garth et al. |
| 8,856,964 | B2 | 10/2014 | Mather |
| 9,008,794 | B2 | 4/2015 | Alexandre |
| 9,204,984 | B2 * | 12/2015 | Brown ..................... A61F 5/01 |
| 9,370,440 | B2 | 6/2016 | Ingimundarson et al. |
| 9,504,595 | B2 | 11/2016 | Josefek |
| 2009/0112129 | A1 | 4/2009 | Lee |
| 2015/0128334 | A1 | 5/2015 | Mazzarolo |
| 2015/0173433 | A1 | 6/2015 | Mazzarolo et al. |
| 2015/0201683 | A1 | 7/2015 | Maud |
| 2015/0297973 | A1 | 10/2015 | Beers |
| 2016/0000640 | A1 | 1/2016 | Lai et al. |
| 2017/0014255 | A1 | 1/2017 | Booker |

FOREIGN PATENT DOCUMENTS

| | | |
|---|---|---|
| CN | 204969518 U | 1/2016 |
| CN | 105495771 A | 4/2016 |
| GB | 245037 | 12/1925 |
| GB | 2352611 A | 2/2001 |
| JP | 2000110016 A | 4/2000 |
| WO | 03051242 A1 | 6/2003 |
| WO | 2009107141 A2 | 9/2009 |
| WO | 2010017667 A1 | 2/2010 |
| WO | 2011047417 A1 | 4/2011 |
| WO | 2012046068 A1 | 4/2012 |

OTHER PUBLICATIONS

On-line sale of "Hooded Top for Squease Inflatable Compression Vest" from funandfunction.com. Retrieved from the Internet Archive "Wayback Machine" from Jun. 30, 2014.
On-line advertisement for "Quatic Inflatable Rashguard" from towsurfer.com. Retrieved from Internet Archive "Wayback Machine" retrieved from Feb. 27, 2015.
"The TruPosture System Senses Bad Posture and Provides Analytics" by Michael Hemsworth, published on Oct. 2, 2015.
Qi, Ziyun, "REInflatable Vest," instructables, instructables.com, Dec. 14, 2014. Retrieved via "Wayback Machine" from Dec. 14, 2014.
EPO Machine Translation of JP2000110016.
English-language abstract of JP2000110016.
English-language abstract of CN204969518.
English-language abstract of CN105495771.
English-language abstract of CN102247021.
English-language abstract of WO2010017667 (integral with WO publication).

* cited by examiner

BACK SUPPORT DEVICE

RELATED APPLICATION

The application claims the benefit of the filing date of provisional application No. 62/343,204 filed on May 31, 2016 and provisional application No. 62/468,504 filed on Mar. 8, 2017. The complete contents of both mentioned applications are incorporated herein by reference to the fullest extent permissible under applicable law.

FIELD OF THE INVENTION

The present invention relates to garments for the upper body, such as, without limitation, shirts, vests, undergarments, coats, and the like, and a device associated therewith which provide selective support for the wearer's back, particularly the spinal column.

BACKGROUND OF THE INVENTION

A significant portion of people suffer from some type of back discomfort or outright pain, particularly in the lower lumbar region, after sitting for an extended period of time, for example, while driving, flying as a passenger, or sitting in a presentation or a lecture. Generally, sitting upright places certain stress on the back because of the effort exerted by the relevant parts of musculoskeletal system to keep a person upright.

One conventional approach to alleviating this problem is the use of various types of external back braces, which generally are wrapped around person's midsection and secured in place when extra back support is desired. Basically, such supports mechanically restrict movement, particularly laterally, of the back such that the muscles of the back can work less hard to keep the back straight. Consequently, however, such back braces usually significantly restrict a user's movement such that it is difficult to easily transition between simply sitting and other activities requiring more mobility and/or freedom of motion. In addition, some conventional back braces are quite bulky or voluminous, and are visually obvious when worn.

Both of these issues usually force a user to put on and take off the conventional back brace repeatedly, depending on need, but this can create a problem in terms of finding a discreet place to put on and take off the brace underneath one's clothing.

Another conventional approach is to use independent cushions or pillows or the like that are manually arranged relative to the desired area of the back, so that the cushion is wedged between the person's back and, for example, a chair back. However, such cushions are prone to shifting if the person moves, requiring frequent repositioning. In addition, such cushions are inherently bulky and are therefore difficult to conveniently carry and store when back support is not needed.

GB 2352611 discloses a selectively inflatable rectangular pad attached to an upper body garment using hook-and-loop strips to permit the pad to be repositioned along a vertical axis of the garment. However, such an arrangement still only provides a limited extent of back support at any given location, and furthermore requires inconvenient changing steps (similar to those associated with a conventional back brace) in order to reposition the pad.

Sometimes an individual suffers from chronic back pain and may also use transcutaneous electrical nerve stimulation (commonly referred to as "TENS") therapy. TENS therapy uses a plurality of flat electrodes that are placed on the skin surface (usually by way of adhesive) in the region requiring therapy, the electrodes transmitting low-strength electrical impulses through the skin. However, it is a recognized problem in a TENS system for the electrodes to lose their adhesive tack relative to the skin, conventionally resulting in a need to frequently replace the electrodes with fresh ones with a new adhesive layer. The costs involved therefore are non-trivial, because the electrodes are typically not inexpensive.

SUMMARY OF THE INVENTION

The present invention relates to a garment worn on the upper part of the body, like a shirt, vest, jacket, pullover, or the like, and a device associated therewith that provides convenient and selective support for the wearer's back region, particularly, but not only, the lumbar region of the back.

Most generally, the garment according to the present invention is provided with a back support system that includes a selectively inflatable cushion or bladder located on a rear-side of the garment in a location where back support is desired. The bladder is inflated when back support is desired, and deflated when back support is not needed or is no longer desired. Characteristically, the bladder is disposed relative to the garment such that when deflated, it is relatively flattened so as to be minimally visible or not visible at all from an exterior of the garment.

In a particular aspect of the present invention, the bladder is particularly shaped to provide specific, or "targeted," support to the back, for example, to a specific region or interval of the spine and/or sacrum as well as support as desired to the musculature of the back adjacent to the spine. In this regard, the bladder according to the present invention may comprise, generally, one or more vertical segments of predetermined length that are positioned in the garment to be generally aligned with and/or in opposition to the wearer's spinal column. As mentioned above, the vertical extent (whether one segment or more than one) of this portion of the bladder may vary and is particularly selectable in order to provide support to a specific portion of the spinal column (i.e., to a certain interval of vertebrae).

In addition, the bladder according to the present invention also includes a plurality of lateral portions (hereinafter referred to as "lobes"). Each lobe extends laterally outward from the vertical segment(s) of the bladder in order to provide desired support for the musculature of the back adjacent to the spinal column. Usually lobes are provided in essentially symmetrical pairs on either lateral side of the bladder, but it is within the scope of the invention to provide a lobe asymmetrically in the bladder (i.e., on one side of the spinal column but not the other).

The shape of each lobe may vary according to the present invention, but it is within the scope of the invention to note that differently shaped (in plan view) lobes may be provided. For example, a basic lobe, example, may be rectilinear in plan, but Applicant has observed that, for example, a rounded (i.e., roughly circular) lobe provides improved support at, for example, the region between the scapulae and the spinal column in the shoulder area, given the anatomical layout of tissues there. The lobes provide relief by supporting a specific part of the musculature rather than providing a general cushion for the back generally. This is akin to the more particular relief of pressing on certain muscles (for example, manually with the heel of the palm) compared to general, overall pressure on the back (for example, when lying on one's back on a mattress).

The entire interior of the bladder may be in contiguous fluid communication such that all parts are either inflated or deflated together, using, for example, a single air inlet/outlet to the bladder.

However, the present invention also contemplates compartmentalizing the respective lobes and vertical segment(s) from one another, such that different parts of the bladder may be selectively inflated and deflated according to user's comfort needs. In that case, each compartment may be provided with a respective air inlet/outlet by which it can be inflated/deflated as desired. It will also be appreciated that this possibility presents an alternative to the possibility mentioned above of asymmetric provision of lateral lobes (i.e., on one side of the spine but not the other). Instead, a pair of symmetrically presented lobes can still be provided, but only one side or the other could be inflated, as desired.

In a secondary aspect of the present invention, the bladder as contemplated is useful in parallel with the use of TENS therapy equipment. Notably, the inflated bladder as contemplated is additionally useful for applying pressure to the TENS electrodes to keep them in required contact with the user's skin, even if the conventional adhesive thereon has deteriorated. The shape of the bladder may be further configured to provide, for example, the lobe portions in locations corresponding to TENS electrode placement on the skin of the back. This is particularly of interest as wireless TENS electrodes become more widely adopted, so that that connecting wires to the electrodes are no longer needed.

In a further aspect of the present invention, the bladder may be provided with one or more pressure sensors adapted to generate a signal to the user if the pressure in the inflated bladder drops below a predefined threshold (i.e., suggesting that the wearing is not sufficiently leaning against the inflated bladder, thereby losing the benefit of back support therefrom). This beneficially reminds the user to alter their seated posture so as to increase their benefit of the inflatable bladder.

BRIEF DESCRIPTION OF THE DRAWINGS

The present invention as described herein will be even more clearly understood with reference to the drawings appended hereto, in which.

It is specifically noted that the figures are not necessarily drawn to scale and are not necessarily visually representative of particular size or other dimension, and principally are intended to illustrate the various elements of the present invention.

DETAILED DESCRIPTION OF THE PRESENT INVENTION

It is noted that the disclosure herein discuss various aspects of the present invention, and all of these aspects or features of the present invention are expressly intended to be combinable to the fullest extent technically possible (e.g., excluding obviously mutually exclusive alternatives), even in the absence of express linking language to that effect.

The present invention is meant to generally relate to garments worn on the upper part of the body in a manner covering the back region, including but not limited to shirts of various types, and thus applies to, without limitation, jackets, vests, t-shirts, coats, undershirts and other kinds of undergarments, etc. If and when used herein, reference is made to "shirts" solely by way of convenient example and without any particular limitation, implied or otherwise, bearing in mind the foregoing.

Figure 1:
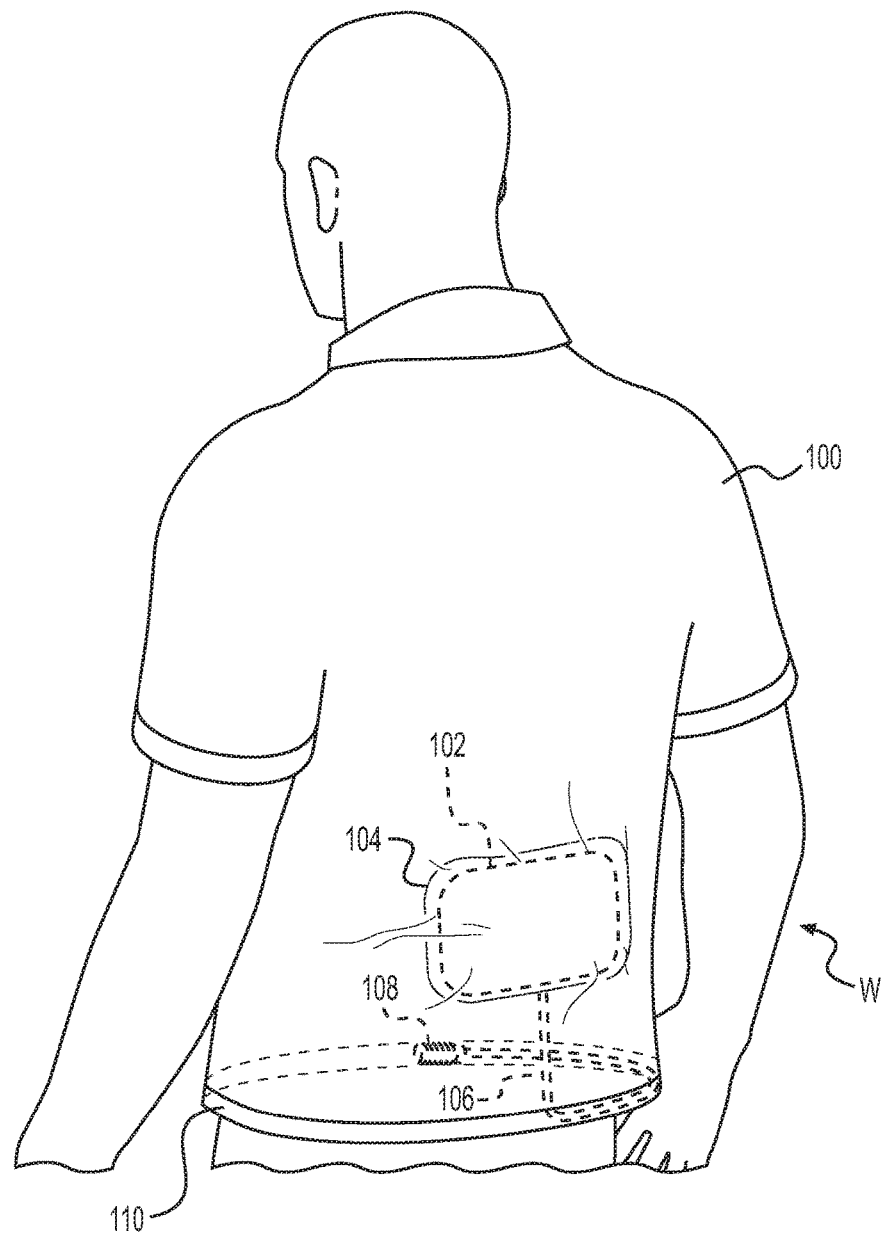
FIG. 1 is an exterior perspective of an example garment into which a first embodiment of the back support system of the present invention is incorporated.
Figure 2:
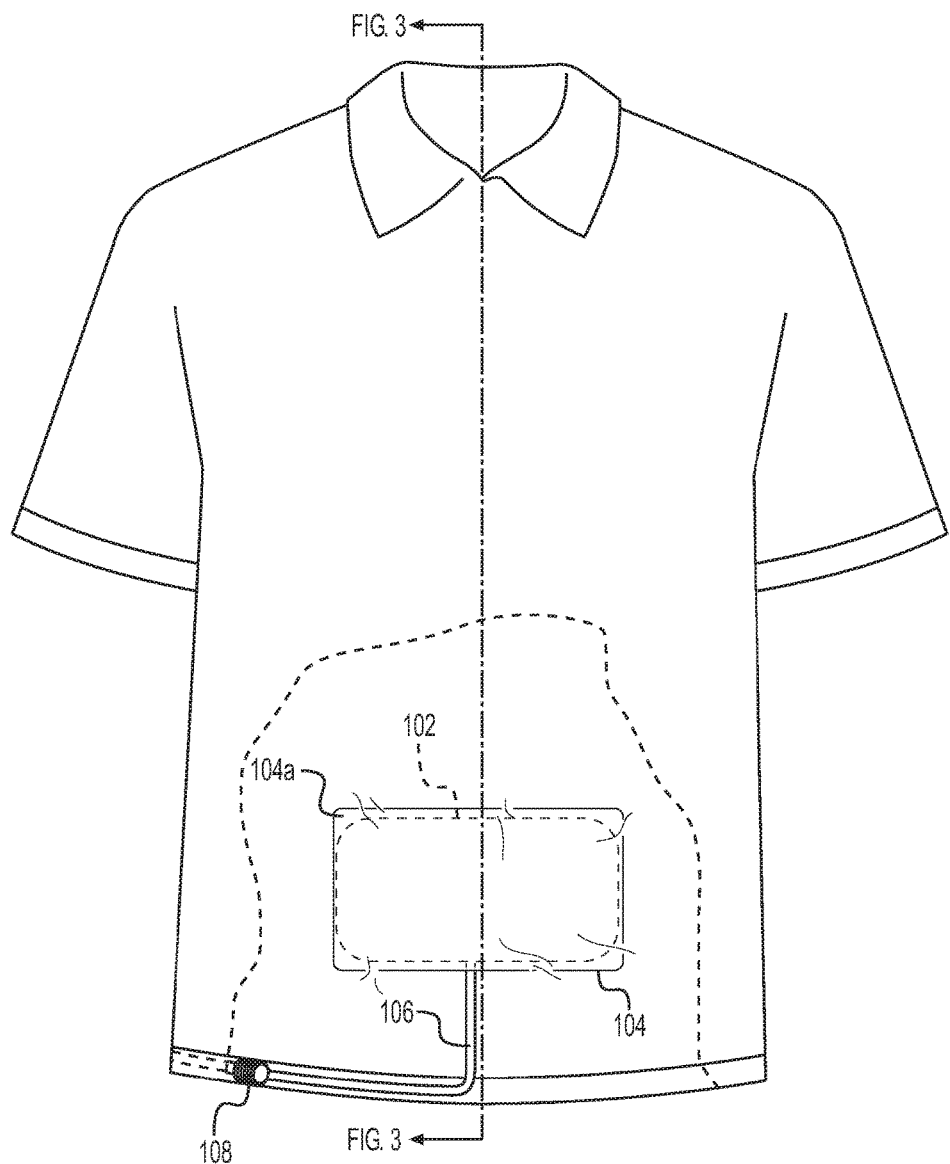
FIG. 2 is a front view of the garment of FIG. 1 in which a portion of the front side of the garment is cut away to illustrate the back support system located at the rear side of the garment.
Figure 3:
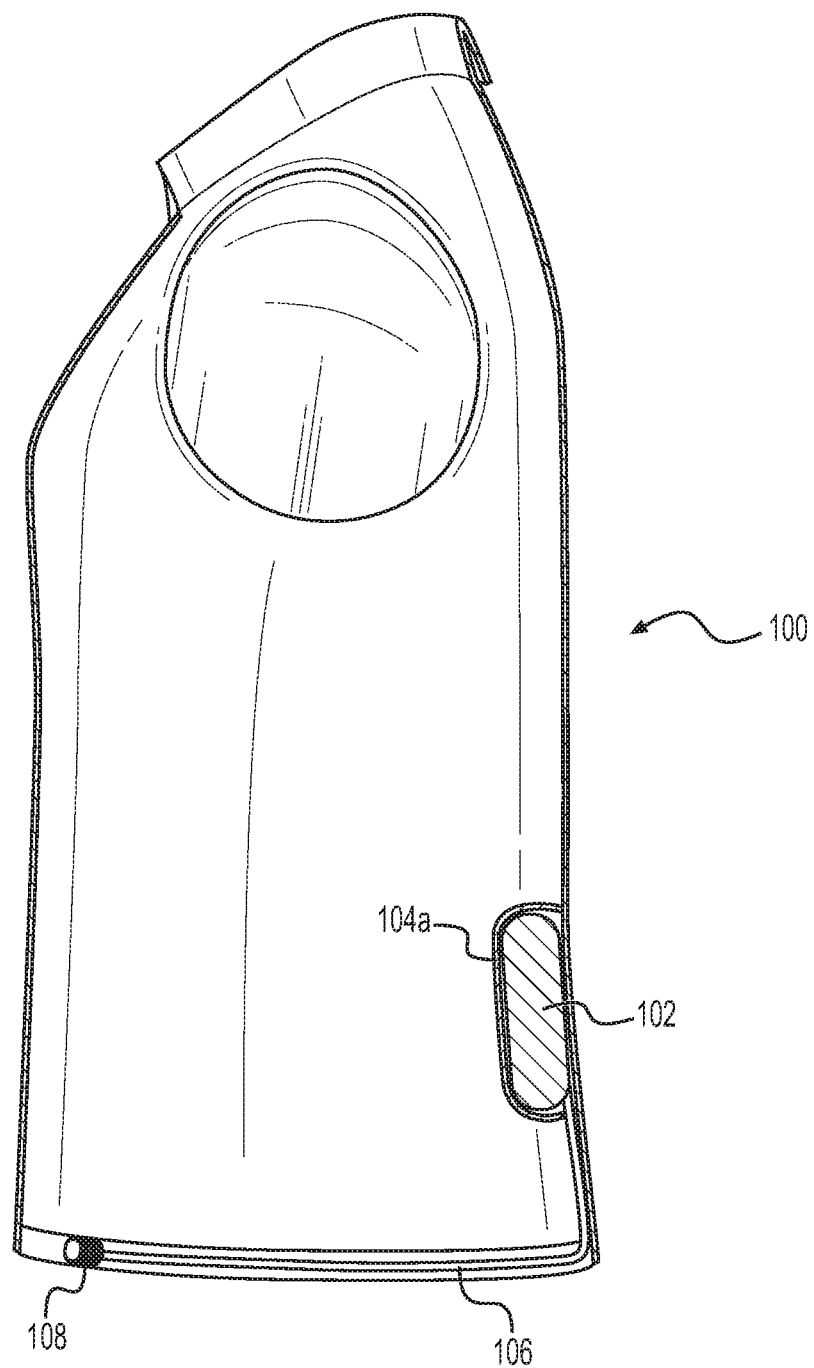
FIG. 3 is a cross-sectional view of the garment of FIG. 2 along line 3-3.

FIGS. 1-3 illustrate aspects of a first embodiment of the present invention.

FIG. 1 is a perspective view of a person W wearing a garment 100 (here, by way of example, a short-sleeve shirt) into which the back support system of the present invention is incorporated.

Generally, the back support system of the present invention includes a selectively inflatable air bladder 102 disposed in a pocket or compartment 104 defined on a rear side of garment 100 at a location where back support is occasionally desired (e.g., at the lumbar region of the back).

The air bladder 102 is inflated (and possibly deflated, as applicable) via a hollow flexible tube 106 connected to and in communication with air bladder 102 at first end and connected to a pump device 108 at a second end thereof, opposite the end connected to air bladder 102.

Preferably, when deflated, the air bladder 102 lies substantially flat relative to exterior surface of garment 100 so as to make it less visible or even invisible from an exterior of the shirt. This can be accomplished in several ways by the construction of the air bladder 102. For example, the air bladder 102 could be constructed from first and second opposing panels (not illustrated) having respective edges that are directly joined to one another at a single peripheral seam (for example, via heat fusing or adhesive), such that in a deflated state, the panels are pressed into contact with one other so that the bladder 102 is flattened. In another example, the air bladder 102 may comprise first and second opposing panels joined by an intermediate peripheral panel extending between the first and second opposing panels and provided with, for example, pre-constructed pleats or folds that promote flattening of the overall air bladder 102 when deflated.

In one example of the present invention, flexible tube 106 extends downwardly from air bladder 102 to a lower hem 110 of the garment 100, and curves laterally therefrom around to a side or a front side of the garment 100, where it connects to pump device 108. In a particular example, the tube 106 may be disposed within hem 110 so as to be at least partly hidden by the material of the garment 100 as it comes around from the rear of the garment (as seen in FIG. 1). The placement of the tube 106 is most generally dictated by minimizing any obstruction or discomfort to the wearer, and by trying to keep the hose minimally visible from perceptible view.

Tube 106 is made from any flexible tubing material that preferably resists kinking (so as to maintain operability of the back support system), such as, without limitation, nylon, rubber, plastic, etc. Tubing similar to that used for air lines in an aquarium as is known (i.e., having, for example, about a 3/16" interior diameter) would be a suitable example. Another suitable example is tubing similar to that used in a conventional sphygmomanometer device having an interior diameter of, for example, about 1/8". If a rubber tubing is used, a non-latex rubber material may be preferable given concerns about latex allergies and sensitivities and the possibility for prolonged skin contact.

The air bladder 102 is selectively inflated via tube 106 using pump device 108 located on the distal end of tube 106. The pump device 108 could be a manually operated pump, operable with a simple manual action such as squeezing a flexible bulb or a bellows-type structure. A piston-type pump could also be used, preferably with a relatively short stroke to maintain the overall compactness of the device.

A preferred manual pump device combines a pump mechanism for inflating the air bladder 102 and a valve device that can be selectively opened to release air from the inflated air bladder 102 so that it can be deflated. In this regard, a flexible bulb/valve assembly of the type commonly used with manually operated sphygmomanometer devices can be used (not illustrated). The assembly has a finger-operated (usually, the thumb and index finger) screw valve that can be tightened/closed to permit inflation by squeezing the bulb, and released/opened (with fingers of the same hand) to permit release of air and deflation of the air bladder 102. Alternatively, the valve may be a bi-direction push button valve (closed when pushed in one direction, open when pushed in the other) that is also easily operated by hand. Examples of bulbs and valves appropriate for the present invention are commercially available from, for example, the Perma-Type Rubber Company of Plainville, Conn., as catalog numbers BULB-01, BULB-02, PPBARV, and MTTAFCV.

The pump device 108 can also be electrically powered, which may provide some advantages in convenience of use. A commercially-available example of a suitable air pump is the Mitsumi R-14 A213 air pump (operating at, for example, 6V and 200 mA), operated by a simple switch or the like. It is lightweight, and has a very low size profile. It is easily powered by equally small commercially available batteries, such as the PX 28 and PX28ab type battery, or the CR2 type battery. An appropriate electric pump generally could operate at, for example, 3, 6, 9, or 12 volts, and preferably weighs less than about 4 oz. The battery (or batteries) and the electric pump can be arranged in electrical connection in a known manner, such as in a cradle or in a housing.

The pump device 108 is preferably sized in a manner that balances pumping efficiency (i.e., permits inflation of the air bladder 102 reasonably quickly without extraordinary pumping action) and compactness (particularly to preserve the aesthetic appearance of the garment when the pump is not in use. In one example of the present invention, the pump device 108 may also be retained in the lower hem 110 of the garment 100, or in a suitably-sized enlarged pocket located in or at the hem 110. Pump device 108 is preferably disposed at a location that permits easy accessibility by the hand used to operate it (i.e., whether for manual operation or for activating a switch on an electric pump), such as along a front side of the garment or at the side thereof (e.g., at the intersection of the front and back panels of the garment 100, if present). Direct manual access to pump device 108 is not necessarily required, if the pump device 108 can be operated through the material of the garment 100.

It is desirable to provide the functionality of the back support system of the present invention while making it aesthetically (particularly, visually) as unobtrusive as possible. In one respect, as mentioned above, air bladder 102 is constructed and arranged to be substantially flattened when deflated. In another aspect, a portion of the flexible tube 106 can be disposed within the hem 110 of the garment 100, as mentioned above, to keep it from being plainly or directly visible from an exterior of the garment. The pump device 108 can also be hidden and enclosed within the material of the garment, as mentioned above.

Also as mentioned above, air bladder 102 is preferably disposed in a pocket or compartment 104 provided at a desired location on the rear side of the garment 100, such as at a location corresponding to the lumbar area of the person W. In one example of the present invention, the pocket 104 is defined by a secondary panel of material 104a (see FIG. 3) attached to the material of the garment 100. Preferably the pocket 104 is sized on the one hand to keep the air bladder 102 in a relatively fixed position and on the other hand to accommodate differences in the size of the air bladder 102 between its inflated and deflated states.

The secondary panel 104a can be attached on an interior or an exterior of the rear side of the garment in order to define the pocket 104 by any conventional attachment means including stitching, heat fusing, etc. In a preferred example of the invention, the secondary panel 104a is attached to an interior side of the rear side of the garment 100, as seen in FIG. 3. In a more particularly preferred example, the secondary panel 104a is glued using a conventional fabric adhesive to the interior surface of the garment 100, particularly so as to avoid the visual traces of stitching that would be visible if the secondary panel 104a were stitched in place. The material of the secondary panel 104a may be the same material as the material of the rest of the garment, particularly if the secondary panel 104a is visible.

Figure 4:
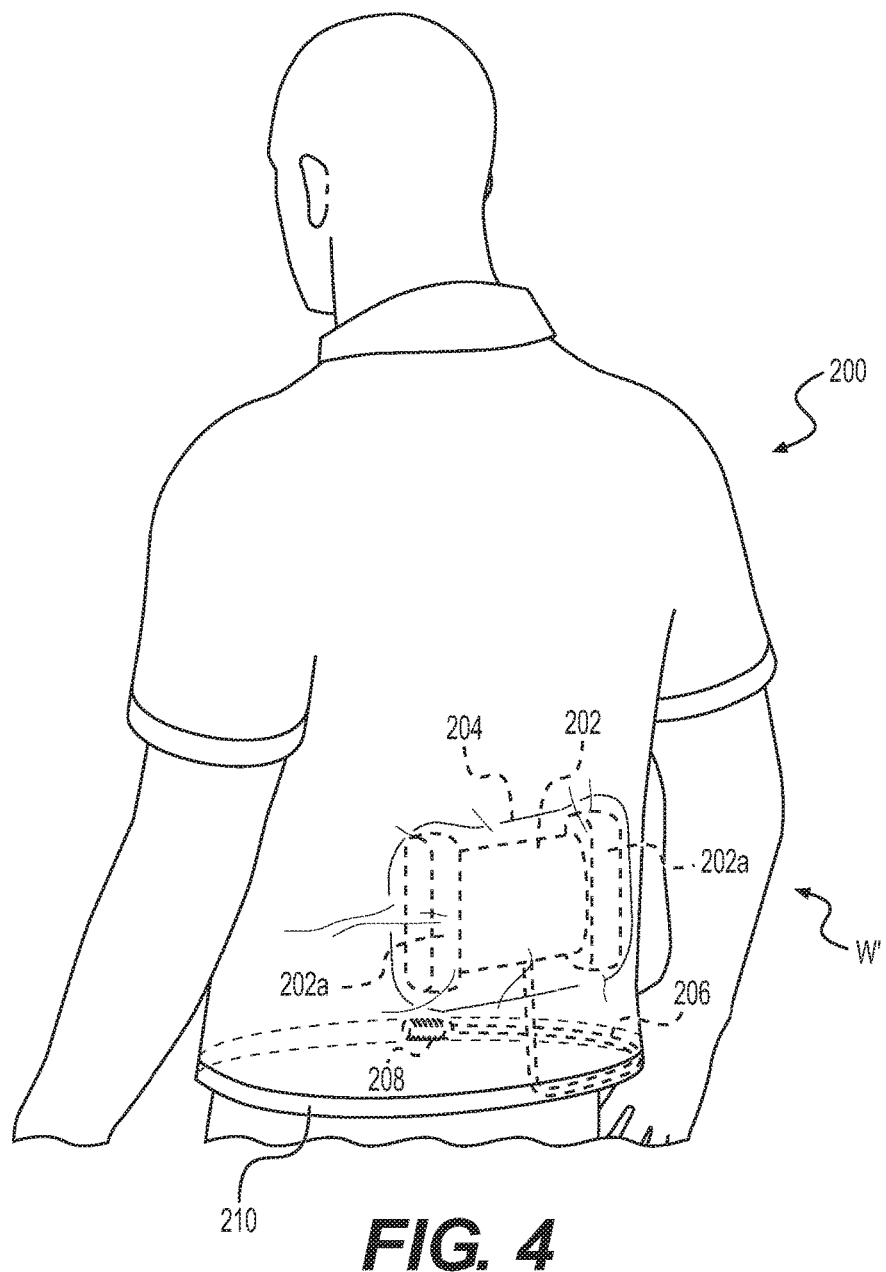
FIG. 4 is an exterior perspective of a garment into which a second embodiment of the back support system of the present invention is incorporated.
Figure 5:
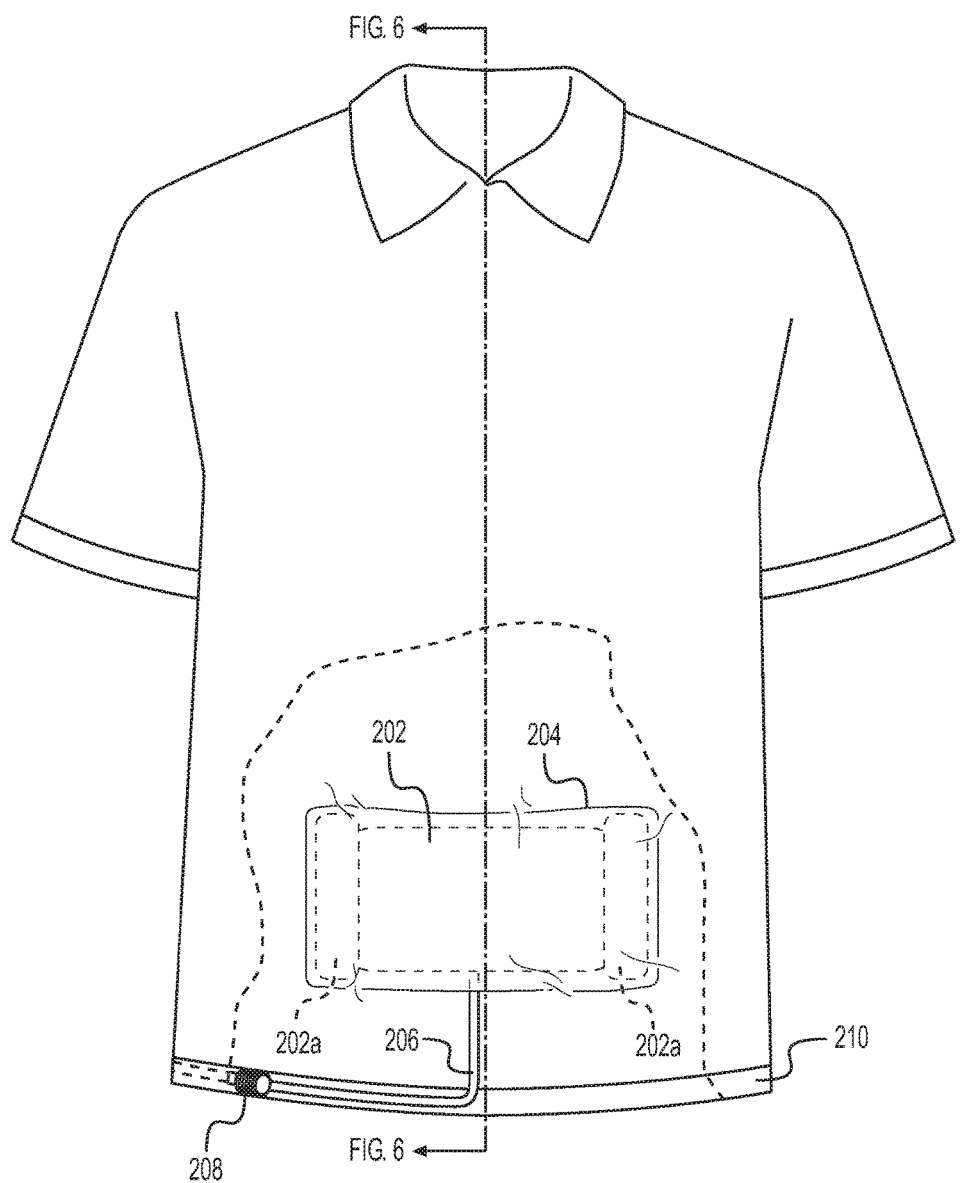
FIG. 5 is a front view of the garment of FIG. 4 in which a portion of the front side of the garment is cut away to illustrate the second embodiment of the back support system located at the rear side of the garment.
Figure 6:
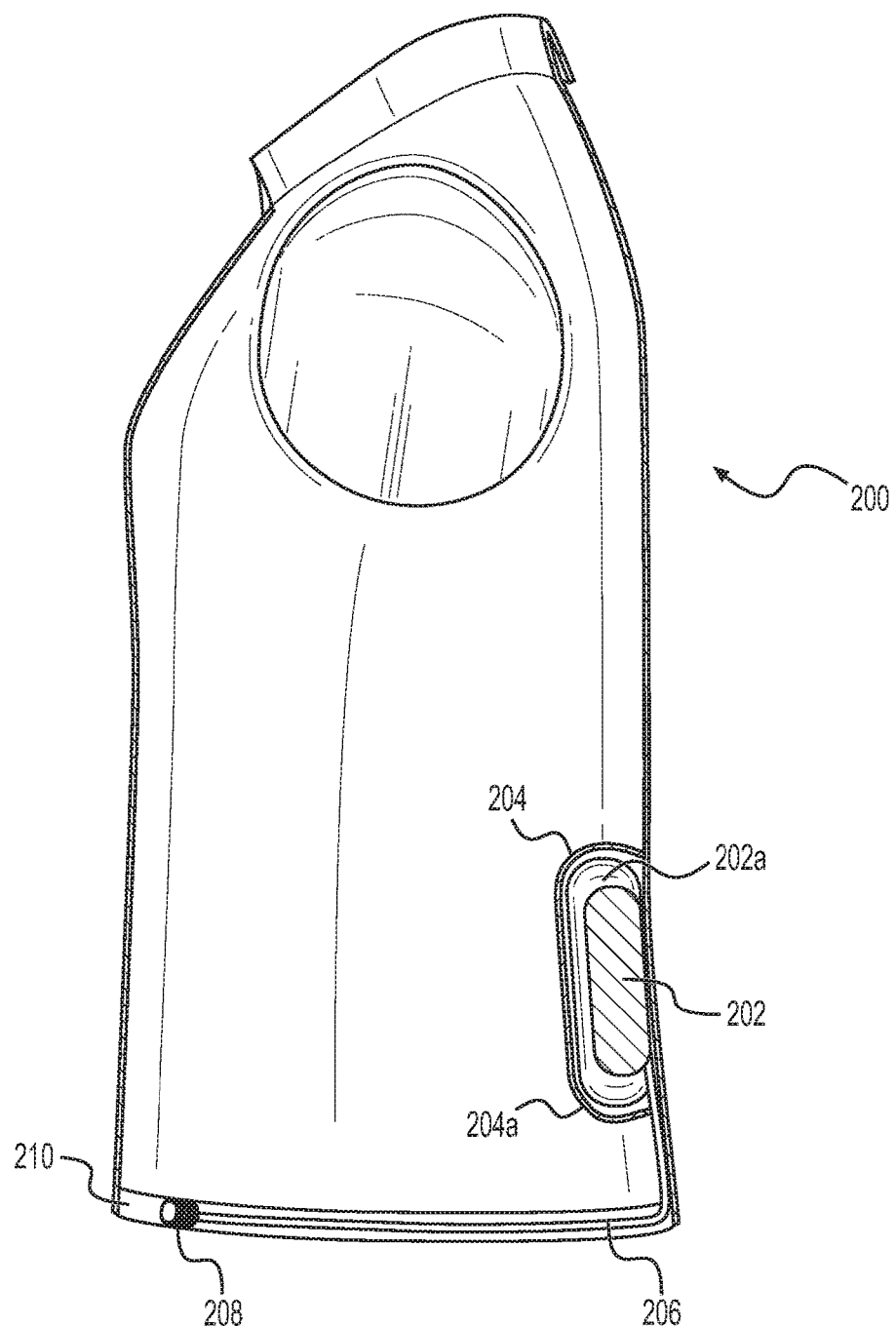
FIG. 6 is a cross-sectional view of the garment of FIG. 5 along line 6-6.

FIGS. 4-6 generally correspond with the views illustrated in FIGS. 1-3, respectively, but show a second embodiment of the air bladder that includes side support lobes 202a at opposite lateral ends thereof. The support lobes provide lateral support to the spine in addition to lumbar support, further easing back strain and fatigue.

FIG. 4 again is a rear perspective view of a person W' wearing a garment 200 (here, again, by way of example, a short sleeve shirt) including the back support system according to the second embodiment of the present invention. As before, a pocket 204 is defined at a lower region of the back of garment 200, in which a selectively inflatable air bladder 202 is disposed. The air bladder 202 of this embodiment characteristically is provided with side lobes 202a at respective lateral ends thereof. The side lobes 202a are generally elongate along a vertical direction of the shirt and are in communication with air bladder 202 so as to be inflated or deflated correspondingly.

In general, the side lobes 202a are spaced generally symmetrically relative to the spine of person W' along a lateral direction. In general, the side lobes 202a provide lateral (side-to-side) support for the spine thereby further reducing back fatigue and discomfort associated with sitting upright for extended periods of time. It is within the scope of the present invention to extend the air bladder 202 in the lateral direction farther than that illustrated in FIG. 4 so that the side lobes 202a are almost at the sides of the body of person W' so that the torso as a whole is provided with lateral support between side lobes 202a. Generally, the side lobes 202a are longer (in the vertical direction of the garment) than air bladder 202 and thicker (in a front-back direction relative to the garment) than air bladder 202, as schematically illustrated in the drawings.

FIGS. 5 and 6 correspond generally with FIGS. 2 and 3, respectively, in terms of points of view, with FIG. 6 being a cross-sectional view taken along line 6-6 in FIG. 5. Corresponding elements, such as flexible tube 206, pump device 208 and secondary panel 204a, all correspond to their counterpart elements in FIGS. 1-3 and the written description of those elements in FIGS. 1-3 apply equally to FIGS. 4-6 with the exception of the details of air bladder 202 and side lobes 202a, as already noted.

In general, the material of air bladder 102/202 and side lobes 202a is a pliable plastic or rubber material that could be made of single material portion or multiple portions of material that are fused or otherwise joined together in a manner sufficient to sustain compressive loads upon the inflated air bladder and/or side lobes. The air bladder and/or side lobes are generally not likely to be subject to sudden compressive forces that would make the internal air pressure spike suddenly and risk causing the bladder to burst. In use, the air bladder and/or side lobes are more likely to be subject to a relatively gradual application of pressure thereon corresponding with a person gradually leaning back against the inflated air bladder and/or side lobes against a chair back or the like. While the material can be expansively resilient to some extent, it is preferable that it not bulge anisotropically or non-uniformly (i.e., more in one direction than another).

It may be desirable in practice to cover or otherwise protect the tube 106/206 and the pump device 108/208 from contact with the wearer's skin, particularly to protect the skin from irritation or chafing. Additional material similar to that from which the garment 100/200 is made could be used for this purpose to the extent needed.

The arrangement of tube 106/206 (leading vertically downward towards the hem 110/210 of the garment 100/200 then around towards a front of the garment) in the Figures is by way of example, and other arrangements are possible. In another example, the tube could extend laterally to a side of the garment (which may or may not have a vertical seam joining front and rear portions of the garment), and downward along the side of the garment.

FIGS. 7-11 illustrate several variants of a third embodiment of the present invention. In general, the third embodiment includes an air bladder generally in accordance with the foregoing description (e.g., with respect to the material of manufacture), but the air bladder structurally comprises one or more vertical (i.e., in vertical direction of the shirt generally aligned with and along the direction of the spinal column) segments and one or more laterally (i.e., extending in a generally horizontal or left-right direction of the shirt, transverse to the spinal column) extending segments (referred to herein as "lobes"). The vertical segments may alternate with the lateral lobes (as in, for example, FIG. 11), or may be contiguous or otherwise intermediate to respective lobes. In this latter sense, strictly speaking, the first and second embodiments also fall within this definition of one or more vertical segments and lateral lobes.

Figure 7:
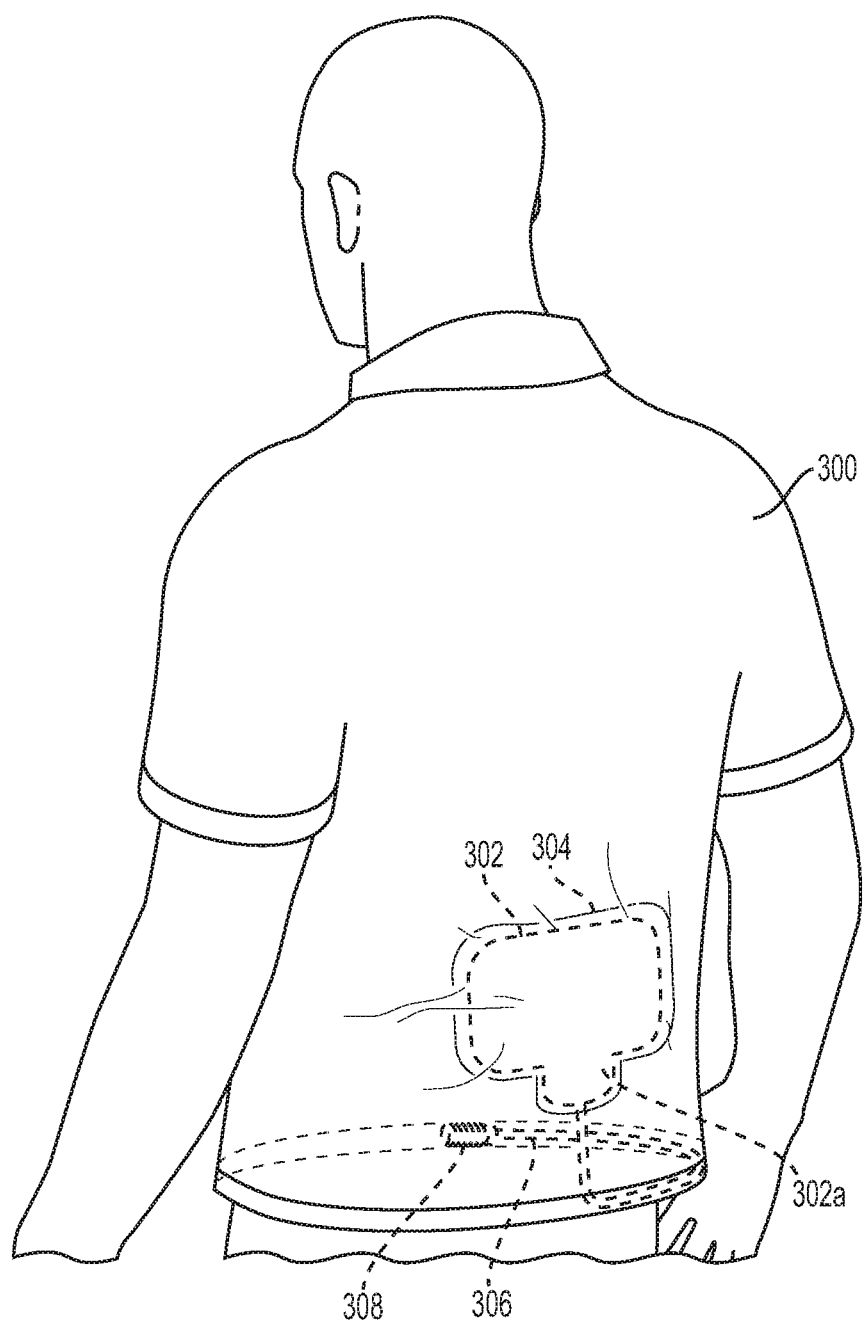
FIG. 7 is an exterior perspective view of a first variant of a third embodiment of the present invention.

FIG. 7 is a rear exterior perspective view of a first variant of third embodiment of the present invention, similar to the views of FIGS. 1 and 4. A garment 300 is provided with an air bladder 302 provided in a pocket 304 defined in the garment in accordance with the description of the first and second embodiments as set forth above. The air bladder 302 is connected to, for example, a flexible tube 306, which tube is in turn connected to a pump device 308. In general, the provision of the flexible tube 306 and pump device 308 is in accordance with the corresponding description of these elements with respect to the first and second embodiments above, in particular with respect to the possibility of using an electric air pump in accordance with the present invention as described in detail above.

Air bladder 302 has a generally rectilinear form similar to that seen in FIG. 1, but includes an additional relatively short vertically extending portion 302a that extends downwardly. When placed in the garment 300, the central part of the rectangular portion of air bladder 302, 302a is positioned relative to the wearer's spine so as to provide lumbar support (i.e., approximately between the L1-L5 vertebrae), and the rectangular portion extends laterally outward to provide support for the quadratus lumborum muscles extending vertically alongside of the lumbar spine (between the ribs and the pelvis). The vertical portion 302a extends downwardly to provide additional support for the sacrum, and is thus relatively short.

Figure 8:
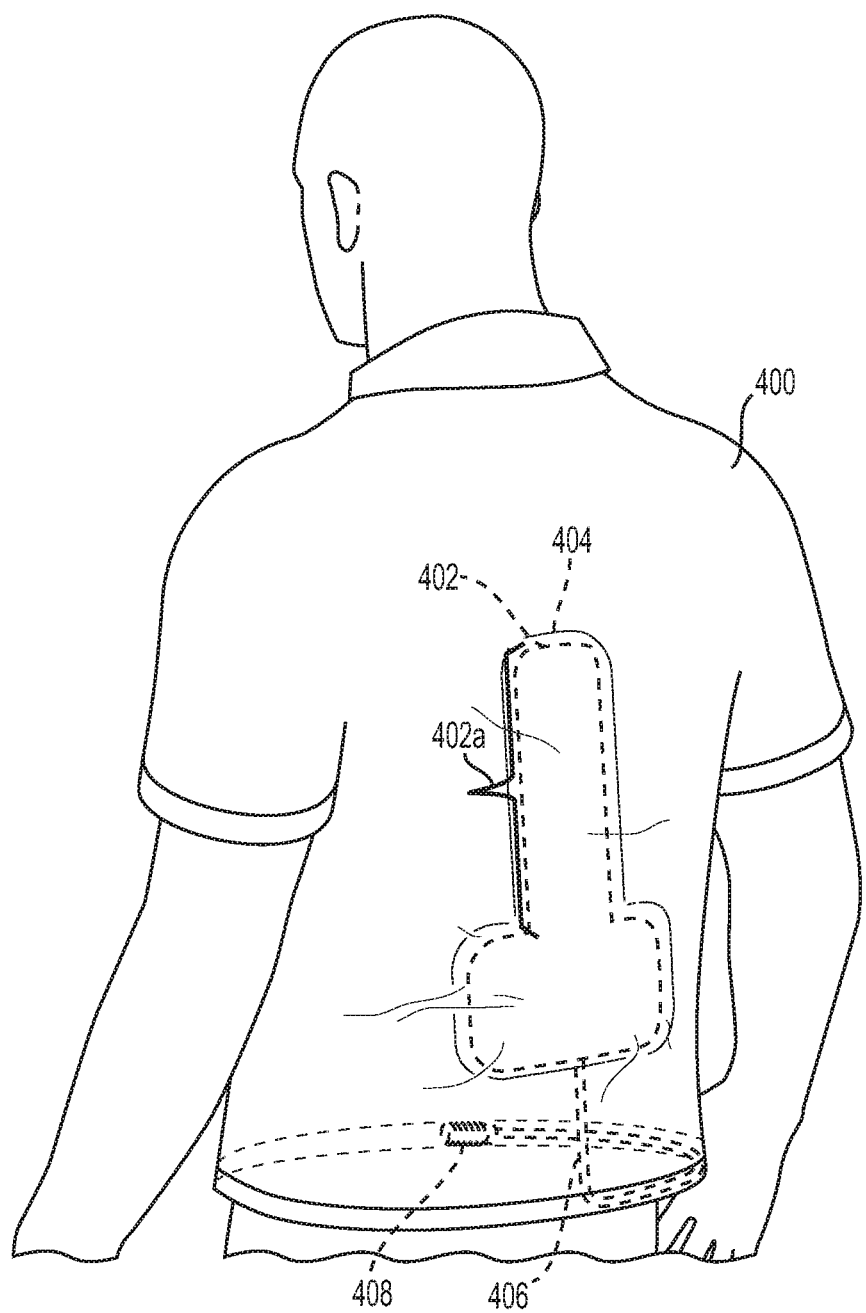
FIG. 8 is an exterior perspective view of a second variant of a third embodiment of the present invention.

FIG. 8 is a second variant of a third embodiment of the present invention, in which an air bladder 402 has a first portion positioned relative to a garment 400 that provides support to the lumbar region of the spine and extends laterally outward to provide support to the quadratus lumborum muscles of the lower back. An additional vertical segment 402a is provided that extends vertically upward along the spinal column to provide additional spinal support up to a lower portion of the thoracic vertebrae (e.g., approximately to the T4 and T5 vertebrae).

The air bladder 402, 402a is connected to a pump device 408 via flexible tube 406 in accordance with the previous discussion above regarding the pump device and flexible tube used in the present invention. The pocket 404 in which the air bladder 402, 402a is received is also in accordance with the description already made hereinabove, except that the shape of the pocket 404 may be formed in general conformance with the shape of air bladder 402, 402a.

Figure 9:
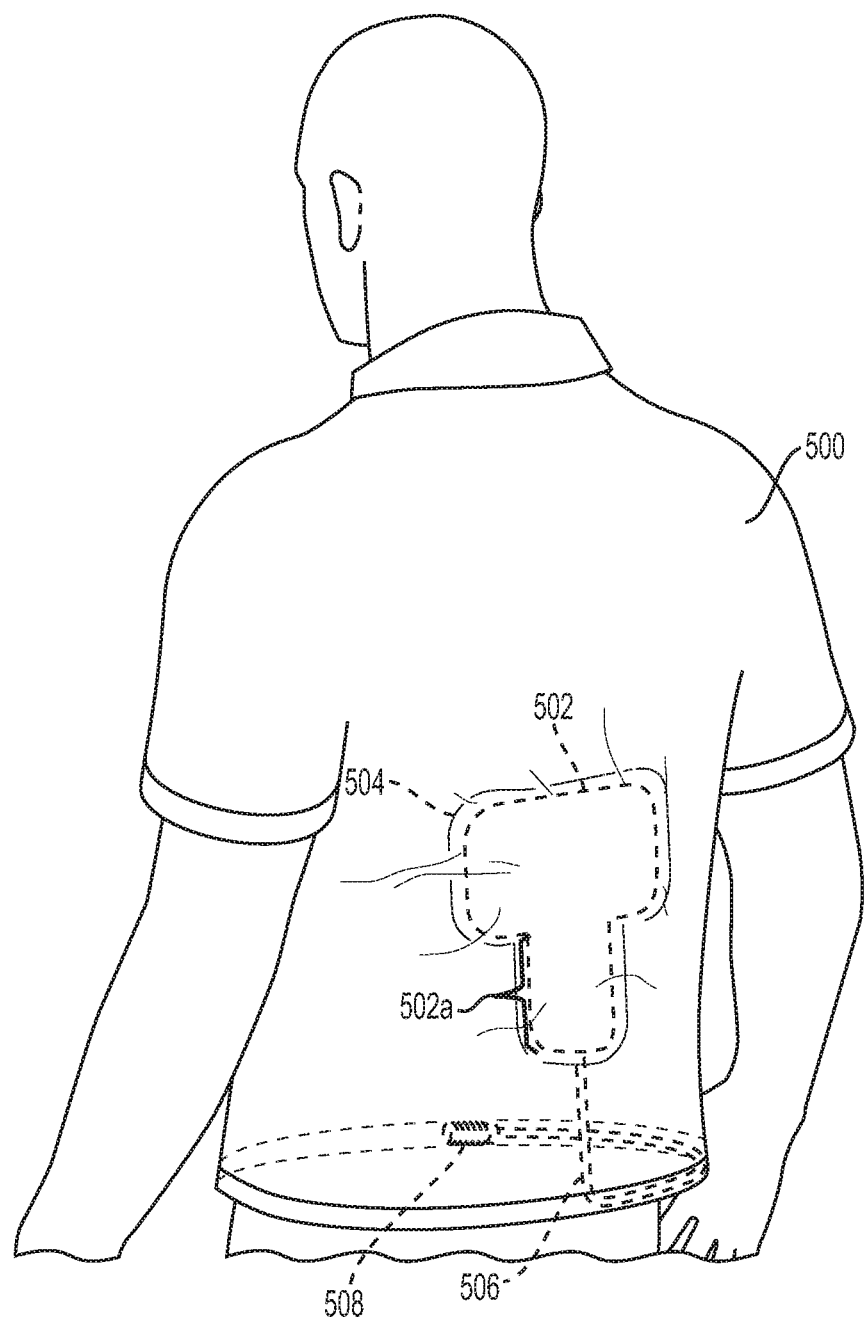
FIG. 9 is an exterior perspective view of a third variant of a third embodiment of the present invention.

FIG. 9 illustrates a third variant of the third embodiment of the present invention. An air bladder 502 has a first portion positioned relative to a garment 500 that provides support to the lower thoracic region of the spine (e.g., the T9-T12 vertebrae) and extends laterally outward therefrom to provide support to the muscles of the erector spinae and the lower trapezius muscles. An additional vertical segment 502a is provided that extends vertically downward along the spinal column to provide additional spinal support for an upper portion of the lumbar vertebrae (e.g., down to approximately the L2-L3 vertebrae).

The air bladder 502, 502a is connected to a pump device 508 via flexible tube 506 in accordance with the previous discussion above regarding the pump device and flexible tube used in the present invention. The pocket 504 in which the air bladder 502, 502a is received is also in accordance with the description already made hereinabove, except that the shape of the pocket 504 may be formed in general conformance with the shape of air bladder 502, 502a.

Figure 10:
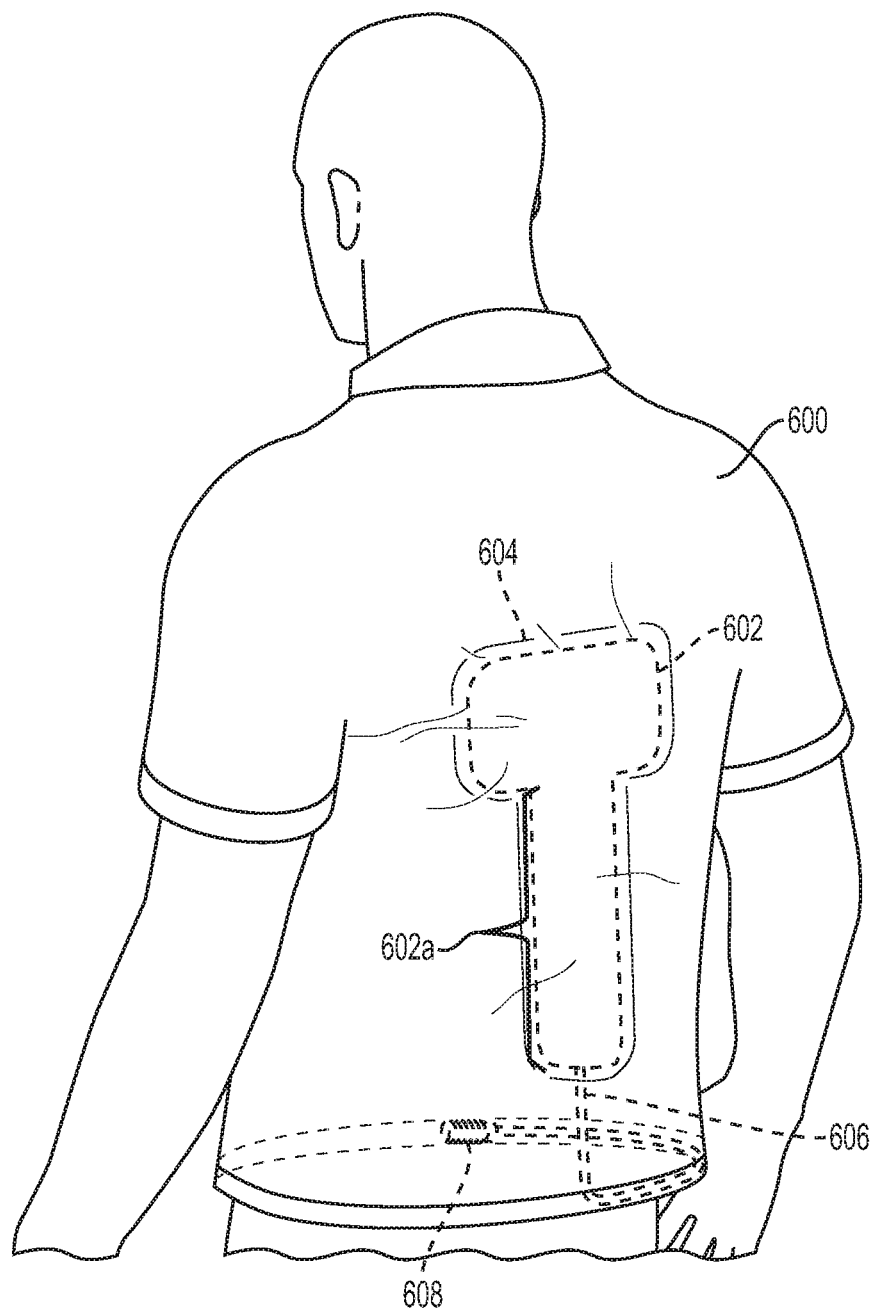
FIG. 10 is an exterior perspective view of a fourth variant of a third embodiment of the present invention.

FIG. 10 illustrates a fourth variant of the third embodiment of the present invention. An air bladder 602 has a first portion positioned relative to a garment 600 that provides support to a mid-portion of the thoracic vertebrae (e.g., the T4-T8 vertebrae) and extends laterally outward to provide support to the muscles of the erector spinae muscles. An additional vertical segment 602a is provided that extends vertically downward along the spinal column to provide additional spinal support for the lower portion of the thoracic vertebrae and an upper portion of the lumbar vertebrae (e.g., from about the T9 vertebrae down to approximately the L2-L3 vertebrae). As such, the vertical segment 602a in FIG. 10 is comparatively longer than vertical segment 502a seen in FIG. 9.

The air bladder 602, 602a is connected to a pump device 608 via flexible tube 606 in accordance with the previous discussion above regarding the pump device and flexible tube used in the present invention. The pocket 604 in which the air bladder 602, 602a is received is also in accordance with the description already made hereinabove, except that the shape of the pocket 604 may be formed in general conformance with the shape of air bladder 602, 602a.

Figure 11:
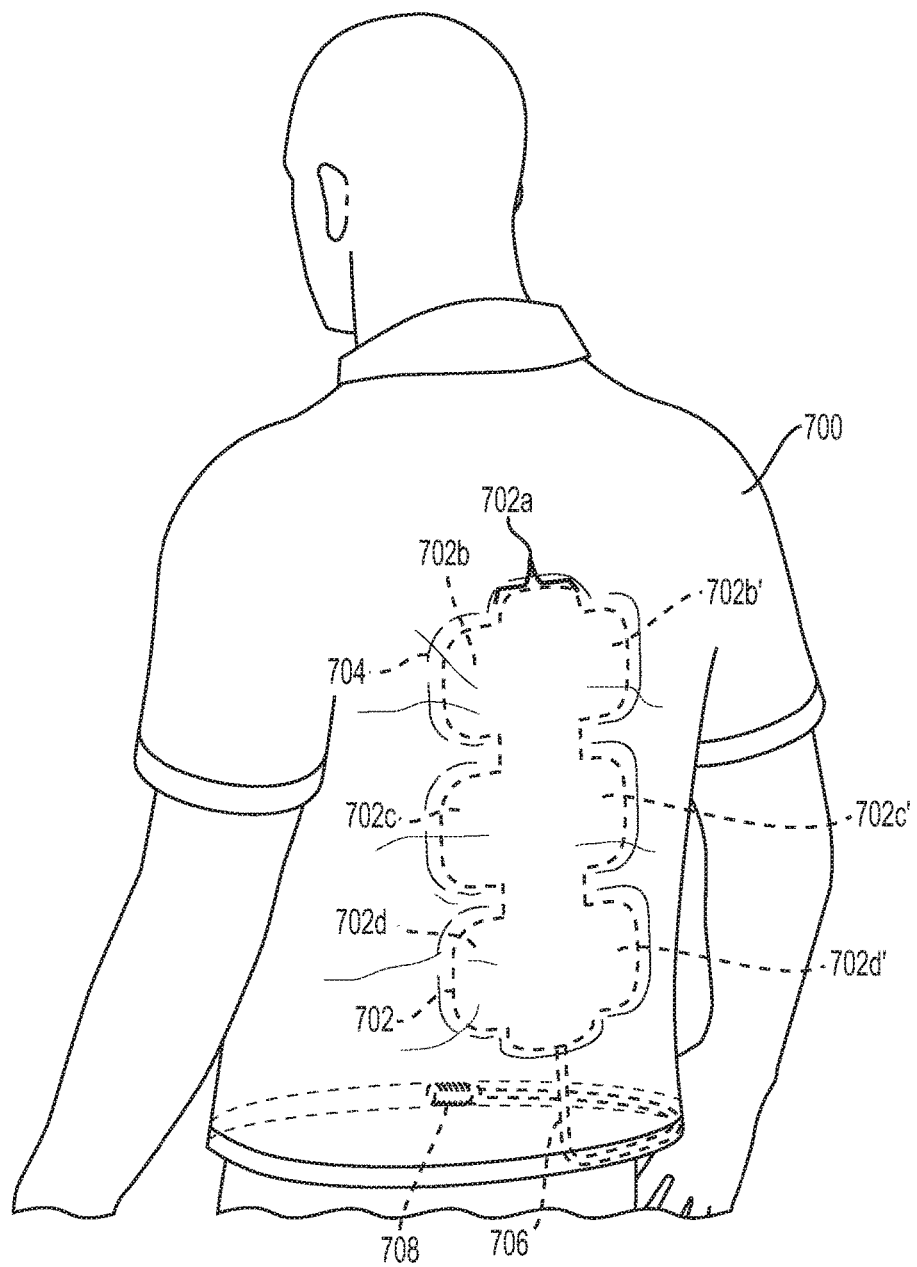
FIG. 11 is an exterior perspective view of a fifth variant of a third embodiment of the present invention.

FIG. 11 illustrates a fifth variant of the third embodiment of the present invention. The air bladder 702 in this example has a relatively more complex form, comprising a vertical segment 702a extending over a relatively major length of the spinal cord, for example, from approximately the T2 vertebrae down to the sacral region of the spine. The air bladder 702 includes, by way of example, three pairs of side lobes 702b, 702b'; 702c, 702c'; and 702d, 702d' on respective lateral sides of vertical segment 702a, each pair of side lobes having a general rectilinear form similar to that seen in FIG. 1, for example. The three pairs of side lobes in FIG. 11 combine the support benefits of those seen in FIG. 8-10, for example, i.e., providing low, mid, and high support for the back musculature, and are located in approximately comparable locations of the shirt as the respective configurations of FIGS. 8-10.

The air bladder 702a; 702b, 702b'; 702c, 702c'; 702d, 702d' is connected to a pump device 708 via flexible tube 706 in accordance with the previous discussion above regarding the pump device and flexible tube used in the present invention. The pocket 704 in which the air bladder 702a; 702b, 702b'; 702c, 702c'; 702d, 702d' is received is also in accordance with the description already made hereinabove, except that the shape of the pocket 604 may be formed in general conformance with the shape of air bladder 702a; 702b, 702b'; 702c, 702c'; 702d, 702d'. It is noted that by way of example, a single flexible tube 706 is used to inflate/deflate air bladder 702a; 702b, 702b'; 702c, 702c'; 702d, 702d'.

Figure 12:
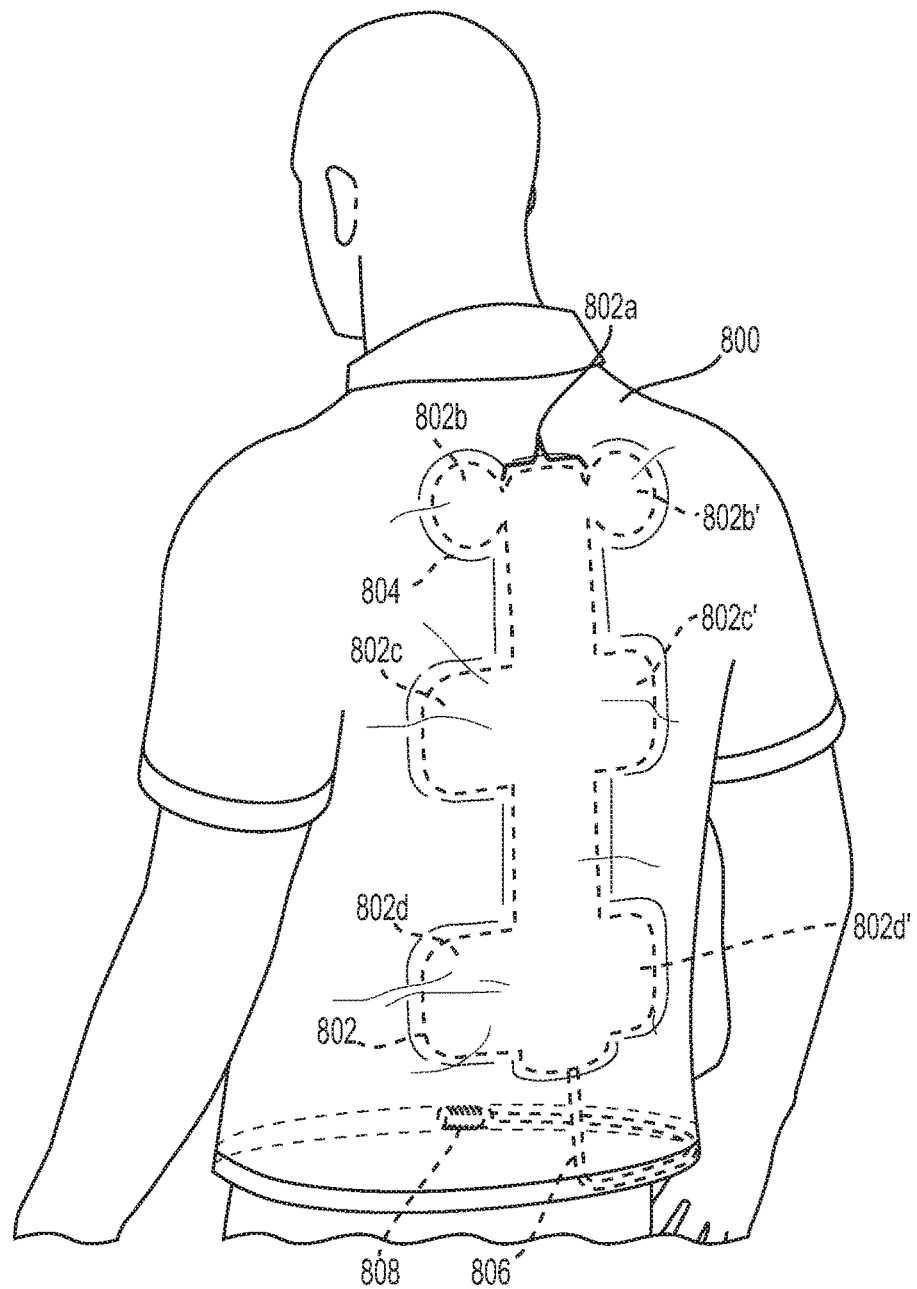
FIG. 12 is an exterior perspective view of a sixth variant of a third embodiment of the present invention.

FIG. 12 illustrates a sixth variant of a third embodiment of the present invention. Air bladder 802 is generally similar in form that air bladder 702 in FIG. 11, except that the air bladder 802 extends farther upward along the back, and side lobe pair 802b, 802b' is notably rounded compared to side lobe pairs 802c,802c' and 802d,802d'. The rounded form of side lobe pair 802b,802b' is believed to provide improved support to the muscles of the shoulder (relative to the shoulder blades) like the infraspinatus and iliocostalis muscles, compared with the rectilinear form of side lobe pairs 802c,802c' and 802d,802d'. The previous corresponding disclosure hereinabove also applies to the pocket 804, flexible tube 806, and pump device 808 in FIG. 12.

Figure 13:
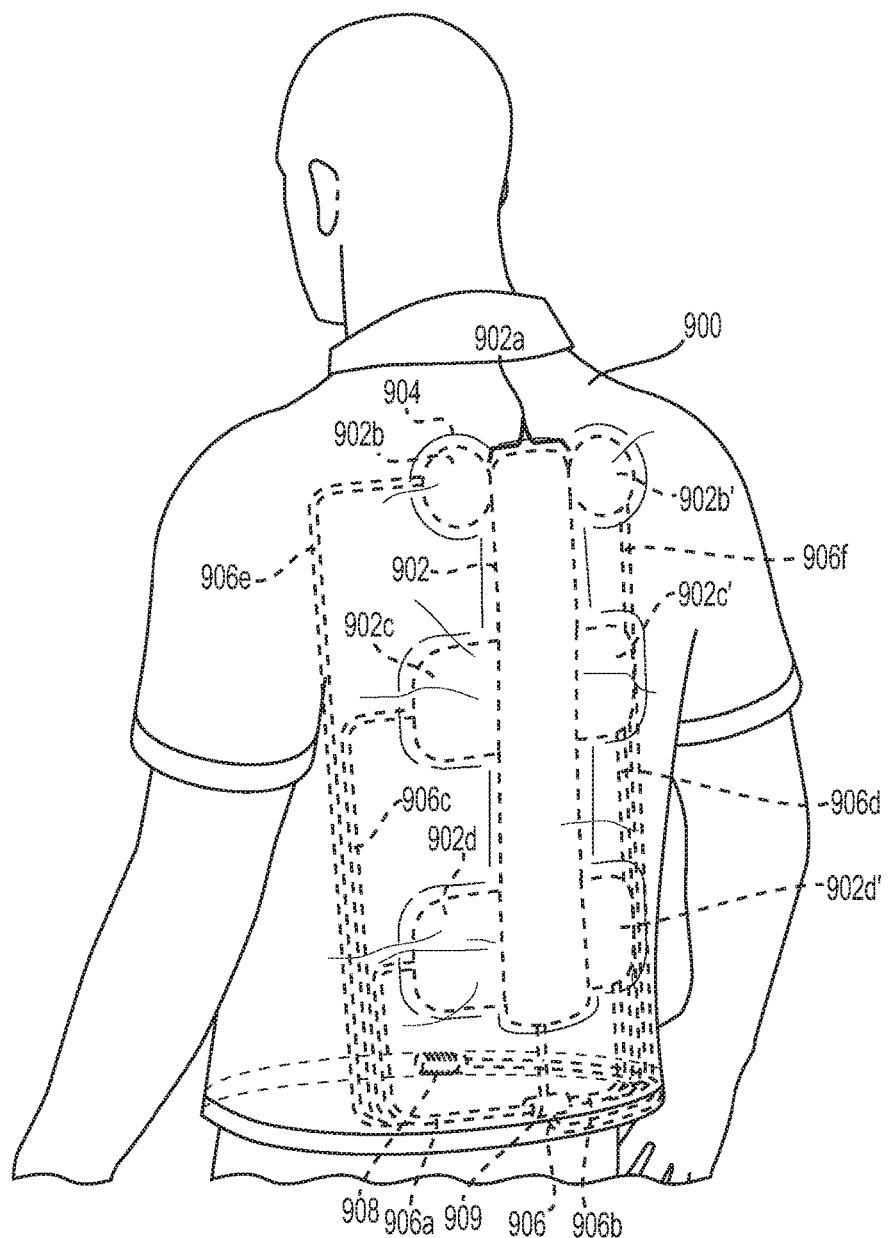
FIG. 13 is a schematic illustration in which the bladder of the third embodiment comprises a plurality of independently inflatable/deflatable portions.

FIG. 13 illustrates a further variant of the present invention, based on the configuration of FIG. 12. Notably in FIG. 13, vertical segment 902a and the side lobes 902b,902b'; 902c,902c'; and 902d,902d' are divided into individual and independent spaces that can be individually inflated or deflated. In general, the various portions can be closed off from one another using one of the processes noted above that is suitable from forming the outer peripheral seam of the air bladder, such as heat fusing. Thus, in FIG. 13, the flexible tubing 906 may be branched at 909 by a conventional fluid branching device (not illustrated in detail here) that provides additional air lines to each compartment of the air bladder 902. Here, only additional air lines 906a and 906b, leading to side lobes 902d and 902d', respectively, are illustrated (in order to maintain the clarity of the illustration), but similar lines are contemplated between the fluid branching device 909 and the other parts (902a; 902b, 902b'; 902c, 902c') of the air bladder 902. The branching device may include respective valve assemblies or the like for each of the branched lines, in order to permit selective inflation of certain parts of the air bladder 902 and not others.

In effect, even the first embodiment shown in FIGS. 1-3 effectively comprises a central vertical segment adjacent to and aligned with the spine, and side lobes provided laterally outward of the vertical segment. The second embodiment of FIGS. 4-6 can also be seen in a similar fashion.

All embodiments of the present invention may be provided with one or more pressure sensors associated with the air bladder. The pressure sensor(s) can be used to provide feedback (e.g., an audible or tactile signal) to the wearer, for example if the detected pressure falls below a given threshold, thereby reminding the wearer to lean against the air bladder more fully, in order to enjoy the benefits therefrom.

In a particular example, this feedback from the pressure sensors can be adapted to indicate where particular parts of the air bladder have insufficient pressure, so that the wearer can particularly adjust his posture in a desirable manner. This idea can be carried further by syncing the pressure sensors with an analytical software package that can aggregate feedback from the pressure sensors relative to a given time period (e.g., a day, week, month, etc.) so that patterns can be identified over time that illustrate posture habits of the wearer, thereby further enabling the wearer to "learn" a better posture. In a preferable example of such a software package, the feedback is visible, for example graphical, in the manner of a color-coded frequency map that visually indicates locations in which insufficient pressure is detected and with what frequency. The data from the pressure sensors is, for example, transmitted wirelessly, using any cost and size appropriate conventional approach, such a Bluetooth wireless transmission. Furthermore, wireless transmission of data from the pressure sensors gives the possibility of reducing the software package to a mobile software application ("app") that can be conveniently implemented on a mobile phone, tablet, smart watch, or other mobile electronic device.

A simple example of such a pressure sensor is a conventional force sensitive resistor (FSR) for detecting the pressure between the wearer and the air bladder. An FSR simply has a variable resistance proportional to the amount its surface is subject to a force thereagainst. The sensor(s) can alternatively be associated with the material/structure of the garment itself, apart from the structure of the air bladder. It should be noted that a quantitative measurement of pressure is possible but not required according to the present invention. Most generally, the pressure of the wearer against the inflated air bladder is considered relative to a predetermined threshold deemed to correspond with ideal or preferred level of support from the air bladder. Thus, the kinds of pressure/force sensors that can be used can include very simple and inexpensive ones. They usually require low levels of power, so they may for example be wired to the power supply for an electric air pump device (when used) or may be connected to small conventional batteries in a known manner, similar to those envisioned for use with an electric pump device as discussed hereinabove.

Instead of providing a single garment structurally associated with a given air bladder configuration, the air bladder, tubing, and pump device could be made portable from garment to garment. For example, at least the air bladder could be provided in a fabric housing or pouch (preferably made from a material that is generally agreeable to skin contact) and provided with a mounting or fastening structure to attach the pouch to an interior of a garment at a suitable position (in accordance with the relationships described herein). For example, the pouch could be zipped into place about a periphery thereof, or conventional hook-and-loop fasteners could be used on an exterior of the pouch and an interior side of the main garment, in a known manner in order to position the air bladder relative to the main garment as required. Conventional snap-fit fasteners could also be used in this regard.

In another aspect of the present invention, rubberized garments are popular in certain fields of endeavor, particularly watersports (water skiing, kayaking, windsurfing, etc.), where neoprene rubber garments are common. Such a garment, adapted to the present invention, could be made using three-dimensional printing technology such that an air bladder in accordance with the present invention could be integrally defined within the rubber material of the garment itself, without the need for a separate air bladder. The description related to FIG. 13 above, in which separate portions of the air bladder can be independently inflated and deflated, is well-suited to this type of construction.

As stated above, the present invention can be applied to a variety of upper body garments. It is noted by way of particular example and without any limitation, that application of the present invention in undergarments or other garments generally worn underneath other garments (undershirts, tank tops, camisoles, etc.) increases a user's flexibility in dressing because the undergarments, outfitted according to the present invention, can be worn with a variety of "main" conventional garments. It also increases the degree to which the physical aspects of the present invention can be generally hidden from view.

Obviously, people, and thus the garments they wear, come in a variety of sizes. Broadly, according to the present invention, the dimensional size of the various configurations of the air bladder contemplated herein can be considered, for example, in terms of the vertebrae and/or associated musculature being targeted, taken in the context of the size of a given garment.

While the present invention is described hereinabove by way of certain examples, it should be clearly understood that the invention as contemplated can be modified while remaining within the ambit of the broad concept of the invention. Again, all features described herein can be used with other features described to the fullest extent possible, even in the absence of specific linking language to that effect.

The invention claimed is:
1. A wearable upper body garment comprising:
a selectively inflatable and deflatable air bladder disposed on a rear side of the garment, the air bladder having an elongate and unitary central portion extending along a vertically-extending center line of the rear side of the garment, and at least one side lobe extending laterally outward from the central portion;
wherein, relative to at least one given direction along the vertically-extending centerline, a distance that the at least one side lobe extends in the given direction is different than a distance that the central portion extends in the given direction;
an air pump device for inflating the air bladder, the air pump device being operably connected to the air bladder by a tube; and
a valve device for selectively retaining air in and releasing air from the air bladder for inflating and deflating the air bladder;
wherein the garment is one of a shirt, a vest, a jacket, a coat, a pullover, a tank top, and a camisole.

2. The garment of claim 1, the air bladder comprising a pair of substantially symmetrical side lobes provided on opposing sides of the central portion of the air bladder.

3. The garment of claim 2, the air bladder comprising at least two of the pairs of side lobes spaced apart from one another along the direction of the center line.

4. The garment of claim 2, the air bladder comprising three of the pairs of side lobes, each pair of side lobes being spaced apart from one another along the direction of the center line.

5. The garment of claim 1, wherein the distance that the central portion extends in the given direction along the centerline is greater than the distance than the distance that the at least one side lobe extends in the given direction.

6. The garment of claim 5, wherein the air bladder comprises a pair of substantially symmetrical side lobes provided on opposing sides of the central portion of the air bladder, wherein the air bladder is located in the garment at a location, for a garment of a given size, substantially corresponding to the L1-L5 lumbar vertebrae and the quadratus lumborum muscles of a wearer having a physical size substantially corresponding to the given size of the garment, wherein the central portion extends downwardly independent from and beyond the pair of side lobes to a location substantially corresponding to the sacrum of the wearer.

7. The garment of claim 5, wherein the air bladder comprises a pair of substantially symmetrical side lobes provided on opposing sides of the central portion of the air bladder, wherein the air bladder is located in the garment at a location, for a garment of a given size, substantially corresponding to the L1-L5 lumbar vertebrae and the quadratus lumborum muscles of a wearer having a physical size substantially corresponding to the given size of the garment, wherein the central portion extends upwardly independent from and beyond the pair of side lobes to a location substantially corresponding to the T4 and T5 thoracic vertebrae of the wearer.

8. The garment of claim 5, wherein the air bladder comprises a pair of substantially symmetrical side lobes provided on opposing sides of the central portion of the air bladder, wherein the air bladder is located in the garment at a location, for a garment of a given size, substantially corresponding to the T9-T12 thoracic vertebrae and the erector spinae and lower trapezius muscles of a wearer having a physical size substantially corresponding to said given size of the garment, wherein the central portion extends downwardly independent from and beyond the pair of side lobes to a location substantially corresponding to L2-L3 lumbar vertebrae of the wearer.

9. The garment of claim 5, wherein the air bladder comprises a pair of substantially symmetrical side lobes provided on opposing sides of the central portion of the air bladder, wherein the air bladder is located in the garment at a location, for a garment of a given size, substantially corresponding to the T4-T8 thoracic vertebrae and the erector spinae muscles of a wearer having a physical size substantially corresponding to the given size of the garment, wherein the central portion extends downwardly independent from and beyond the pair of side lobes to a location substantially corresponding to the L2-L3 lumbar vertebrae of the wearer.

10. The garment of claim 5, wherein the air bladder comprises three pairs of substantially symmetrical side lobes provided on opposing sides of the central portion of the air bladder and being spaced apart from each other along the center line of the garment, wherein the air bladder is located in the garment at a location, for a garment of a given size, so that the central portion extends substantially in opposition to approximately the T2 thoracic vertebrae down to the sacrum of a wearer of the garment, where the wearer of the garment has a physical size substantially corresponding to the given size of the garment.

11. The garment according to claim 10, wherein each side lobe of an uppermost pair of side lobes extends laterally outward from the central portion and has an at least partly circular form taken substantially in the plane of the rear side of the garment and is located in the garment at a location, for a garment of a given size, so as to oppose the infraspinatus and iliocostalis muscles of a wearer having a physical size substantially corresponding to the given size of the garment.

12. The garment of claim 1, wherein the at least one side lobe extends laterally outward from the central portion and has an at least partly circular form taken substantially in the plane of the rear side of the garment.

13. The garment of claim 1, wherein the air bladder is disposed within a pocket defined in the rear side of the garment.

14. The garment of claim 13, wherein the pocket is defined by a material portion attached to an interior side of the garment to define the pocket between the material portion and the interior side of the garment.

15. The garment of claim 14, wherein the material portion is stitched to the interior side of the garment.

16. The garment of claim 1, wherein air pump device, the tube connecting the air pump device and the air bladder, and the valve device are attached to the garment in a manner so as to be at least partially hidden from view from an exterior of the garment.

17. The garment of claim 16, wherein the garment includes a lower peripheral hem at a bottom edge thereof, and one or more of the air pump device, the valve device, and at least a portion of the tube connecting the air pump device and the air bladder are disposed within the peripheral hem.

18. The garment of claim 1, wherein the air pump device comprises an electrical air pump device operably connected to battery power source.

19. The garment of claim 1, wherein the air bladder is associated with at least one pressure sensor constructed and arranged to detect a force applied to the air bladder when inflated and to provide a perceptible signal when the detected force falls below a predetermined threshold.

20. The garment of claim 1, wherein the extent of the central portion of the air bladder along the center line of the garment provides support when inflated to a combination of two or more of the thoracic vertebrae, the lumbar vertebrae, and the sacrum.

21. The garment according to claim 1, wherein the garment is made from a rubber material, wherein the air bladder is integrally defined within the rubber material of the garment.

22. The garment according to claim 21, manufactured by a three-dimensional printing process using a rubber material to thereby define the air bladder.

23. The garment according to claim 1, wherein the garment is a shirt, and the shirt is one of polo shirt, an undershirt, and a t-shirt.

24. An inflatable back support device comprising:
a selectively inflatable and deflatable air bladder, the air bladder having an elongate and unitary central portion extending along a center line, and at least one side lobe extending laterally outward, relative to the center line, from the central portion;
wherein, relative to a given direction along the center line, a distance that the at least one side lobe extends in the given direction is different than a distance that the central portion extends in the given direction;
an air pump device for inflating the air bladder, the air pump device being operably connected to the air bladder by a tube; and
a valve device for selectively retaining air in and releasing air from the air bladder for inflating and deflating the air bladder.

25. The device according to claim 24, wherein at least the air bladder is housed in a casing.

26. The device according to claim 25, wherein an exterior of the casing includes a fastening mechanism constructed and arranged to engage a cooperating mechanism provided on an interior rear side of a wearable upper body garment so as to positionally fix the device relative to the garment, wherein the garment is one of a shirt, a vest, a jacket, a coat, a pullover, a tank top, and a camisole.

27. A method of providing selective back support for an individual seated in a seat having a seat back and wearing a garment comprising a selectively inflatable and deflatable air bladder disposed on a rear side of the garment opposite a selected region of the individual's back;
wherein the air bladder has an elongate and unitary central portion extending along a vertically-extending center line of the rear side of the garment and generally aligned with the individual's spinal column, and at least one side lobe extending laterally outward from the central portion;
wherein, relative to at least one given direction along the vertically-extending centerline, a distance that the at least one side lobe extends in the given direction is different than a distance that the central portion extends in the given direction;
the method comprising:
selectively inflating the air bladder; and
leaning against the seat back so as to press the selectively inflated air bladder between the seat back and the individual's back, until a desired level of air pressure is generated within the air bladder, the desired level of air pressure corresponding to a desired level of back support for the individual.

28. The method of claim 27, wherein the air bladder includes an elongate and unitary central portion extending along a vertically extending center line of the rear side of the garment, and at least one pair of side lobes, each side lobe of the at least one pair of side lobes extending laterally outward from the central portion in generally opposite directions, wherein selectively inflating the air bladder comprises one part of the air bladder to a different air pressure than a remaining part of the air bladder.

29. The method of claim 27, further comprising dynamically detecting an air pressure in the air bladder, and signaling the wearer if the detected air pressure is below a predetermined threshold.

30. The method of claim 29, wherein detecting an air pressure in the air bladder comprises detecting a plurality of air pressures corresponding respective ones of the central portion and the at least one side lobes.

* * * * *